United States Patent [19]

Corey et al.

[11] 4,304,675
[45] Dec. 8, 1981

[54] ANTISTATIC ZEOLITE COMPOSITION AND METHOD FOR DEODORIZING RUGS AND ROOMS

[75] Inventors: Garland G. Corey, Milltown; Leon E. Paszek, Mountainside, both of N.J.

[73] Assignee: Sterling Drug Inc., New York, N.Y.

[21] Appl. No.: 107,317

[22] Filed: Dec. 26, 1979

[51] Int. Cl.$^3$ ............................................. D06M 11/04
[52] U.S. Cl. ......................................... 252/8.6; 252/90; 252/506; 252/11; 252/455 Z; 424/76; 8/137.5; 8/142
[58] Field of Search .................. 252/8.6, 135, 90, 506, 252/11, 455 Z; 424/76; 8/137.5, 142

[56] References Cited

U.S. PATENT DOCUMENTS 4,161,449 1/1979 Smith et al. ........................ 252/8.6

OTHER PUBLICATIONS

Chemical Abstracts, vol. 46:11542e; 65:14901b; Dec. Index, p. 24,412S, vols. 56–65; vol. 84:35065m, 35101v.

*Primary Examiner*—John D. Welsh
*Attorney, Agent, or Firm*—Wenderoth, Lind & Ponack

[57] ABSTRACT

A method and composition for deodorizing rugs is provided herein by applying a non-free flowing powder-fragrance composition onto a carpet and subsequently removing the composition, preferably by vacuuming. The invention also includes a package in the form of a shakeable canister for applying to rugs the aforementioned non-free flowing powder-fragrance composition. The non-free flowing powdered composition is made up of essentially an inorganic salt, such as sulfate, a chloride or bicarbonate or mixtures thereof, a fragrance, an antistatic and rheological control agent selected from natural and synthetic zeolites, and a liquid agglomerating agent. The composition exhibits stable non-free flowing properties, even at elevated temperatures, over a long period of time.

16 Claims, No Drawings

ANTISTATIC ZEOLITE COMPOSITION AND METHOD FOR DEODORIZING RUGS AND ROOMS

BACKGROUND OF THE INVENTION

The present invention relates to a method and composition for deodorizing rugs and rooms by applying a nonfree flowing powder-fragrance composition onto a carpet and subsequently removing the powdered composition from the carpet. The composition also imparts other attributes to the carpet including antistatic and anti-soiling effects. The invention also includes a package in the form of a shakeable canister for applying to rugs the aforementioned non-free flowing powder-fragrance composition.

In practice, it is desirable to apply powdered fragrance compositions, including the powdered composition of the present invention, onto the rugs by means of a shakeable canister containing openings at the top thereof and then to remove the composition by means of a vacuum cleaner. In such a method, not only is the deodorizing effect of the fragrance composition imparted directly to the rug, but the vacuuming process itself provides deodorizing or air freshening properties to the surrounding atmosphere. This is because the fragrance composition is spread throughout the carpet during the vacuuming and also some of the fragrance is exhausted into the atmosphere by the vacuum cleaner. Thus, the carpet, room and vacuum cleaner play an integral part in deodorization.

DESCRIPTION OF PRIOR ART

Prior to the present invention, compositions and methods for deodorizing carpets and rooms and imparting other characteristics to carpets have been well known. One such composition is disclosed in U.S. Pat. No. 4,161,449 issued to Smith et al on July 17, 1979. Smith et al described their powdered deodorizing composition for carpets as comprising an inorganic carrier such as a sulfate or chloride of a specified particle size range, a solid agglomerating agent such as starch, a fragrance and optionally up to 15% of an antistatic agent, preferably aluminum oxide. An important object of the Smith et al patent is the production of a powder which is not overly dusty and which will not be scattered too readily into the atmosphere during the vacuuming process and at the same time is not so agglomerated or coarse that the efficient removal of the product from the carpet is prevented.

The above-described Smith et al composition has various disadvantages. Thus, while the Smith et al composition may be described as a non-free flowing composition or "lazy" powder which can be dispensed from shakeable container in controlled amounts, the composition suffers from the disadvantage that the flow or rheological properties of the composition are not stable over a long period of time, particularly at elevated temperatures. This is a serious shortcoming in that the product must sometimes be stored in a warehouse or transported under conditions where the temperature may be as high as about 120° F. and if the non-free flowing characteristics are deteriorated (i.e. the composition approaches a free flowing powder), this represents a great disadvantage to the consumer.

Another disadvantage of the smith et al composition is that when aluminum oxide is used in the composition (and this material is apparently preferred), certain fragrance materials will color the aluminum oxide, which makes the product unsightly. The zeolite component of the present invention is not subject to such disadvantage.

A further shortcoming of the Smith et al composition is that the particle size of the carrier component must be carefully controlled, whereas the particle size of the ingredients of the present invention need not be so limited.

OBJECTS OF THE INVENTION

An object of this invention is to provide non-free flowing powder-fragrance composition which exhibits satisfactory flow or rheological properties so that the material may be dispensed from a shakeable canister in controlled amounts, i.e., the powdered composition should be such that when shaken from the container, it should not be entirely free-flowing so that it is dispensed all in one spot on the carpet and on the other hand should be capable of being dispensed onto the rug in adequate amounts to impart satisfactory deodorizing or air freshening characteristics thereto.

Another object of this invention is to provide a non-free flowing powder-fragrance composition which has controlled rheological or flow properties over a long period of time and at varying temperatures so that the flow characteristics of the powdered composition remain stable.

Still another object of this invention is to provide a composition which has excellent fragrance retaining properties, but which when transferred to a carpet gives off the fragrance relatively fast as opposed to prior art compositions.

Another object of the present invention is to provide a composition which when applied to a carpet during the vacuuming process imparts excellent deodorizing, antistatic and anti-soiling effects.

Another object of the invention is to provide a method for deodorizing rugs and room using the non-free flowing powder-fragrance composition of the invention.

A still further object is to provide a package in the form of a shakeable canister having openings at the top and containing the non-free flowing powder-fragrance composition referred to in the above-mentioned objects.

Various other objects and advantages of this invention will be apparent from the following description.

GENERAL DESCRIPTION OF THE INVENTION

It has been found that the objects of the invention may be realized by providing a powdered carpet treating composition containing a particular type of inorganic material, namely natural and synthetic zeolites that have a capacity to adsorb liquid systems and regulate the rheological properties of the powder composition. In accordance with the present invention, it has been found that the aforedescribed carpet treating composition has stable rheological or flow properties over a long period of time, which composition imparts excellent deodorizing or air freshening attributes to carpets and rooms.

The zeolite material used in accordance with this invention also imparts antistatic and anti-soiling properties to the composition, such that when applied to carpets a significant reduction of static electricity occurs and antisoiling effects are observed.

The zeolite materials by themselves or in combination with the other important ingredients to be discussed below may be used to "load" liquids ranging from water to organic liquids, including fragrance compounds or components, antistatic agents, subliming agents, antimicrobial agents, cleaning agents and fragrance volatility control materials. The only qualification for the liquid system to be loaded is that the liquid does not react with the other materials of the composition so as to destroy their physical and chemical properties. Preferably, the pH of the liquids system be greater than 6 and less than 10.

More particularly, the present invention relates to a powdered carpet treating composition having stable rheological properties consisting essentially of a blend of:

(a) a major amount in respect to each of the individual components in the composition of an inorganic salt selected from the group consisting of sulfates, bicarbonates, chlorides and mixtures thereof;

(b) an effective deodorizing amount of a fragrance;

(c) an antistatic and rheological control agent selected from the group consisting of natural and synthetic zeolites, said material being used in an effective amount sufficient to impart antistatic properties to the composition and control the rheological properties of the composition; and (d) an effective agglomerating amount of a substantially non-fragrant liquid agglomerating agent.

In the above composition, the weight ratio of component (c) to component (d) is generally from between about 30.0:1.0 to about 0.5:1.0.

It has been found that desirable results are obtained with the carpet treating compositions of this invention when the critical flow value is from about 5.0 to about 30.0 g when stored in a closed container at temperatures up to 120° F. for at least 30 days.

The "critical flow value" is measured by perceiving the rate of flow of the composition through a specified series of openings from a given size container at a given fill. Specifically, 100 g of the composition is filled into a container 2.5" in diameter by 5.5" in height, having four holes, each approximately 0.31" in diameter enscribed in a 1" circle. The container is inverted successively five times and the amount of material dispensed is determined. The critical flow value is therefore a measure of the rheological properties of the composition.

The composition may be considered stable if the critical flow value is about 30% or less when measured according to the aforementioned test at a specififed temperature. The composition of the present invention has stable rheological properties at temperatures up to about 120° F. for a minimum of 30 days, which is a decided advantage as opposed to prior art compositions of the type described in U.S. Pat. No. 4,161,449 to Smith et al.

The effective fragrance imparting properties of the composition also is maintained for at least 30 days when stored in a closed container at temperatures up to about 120° F.

One of the advantages of the present invention is that the composition is able to retain the fragrance or perfume when stored in a container at a given temperature in a "neat" condition. The powdered composition of the present invention tends to "hold" those fragrances which have higher volatility parameters than powdered compositions which unstable rheological properties. However, when the powdered deodorizing compositions of the invention are sprinkled from the container onto carpeting, the composition tends to given up the fragrance more readily than other compositions, such as the aluminum oxide containing compositions described above.

The "lazy" (non-free flowing) powder of the present invention is characterized in that in use, the product must be shaken from the container using a side-to-side motion.

If the container is accidentally inverted, the flow will stop due to the bridging properties of the powder in which the holes on the top of the container are temporarily clogged up with powdered agglomerates.

This "bridging" phenomenon therefore functions like an automatic valve which stops the flow of the powder when the container is inverted. To continue the flow it is necessary to shake the product from the container using a side-to-side motion thereby making it possible to dispense the product in controlled amounts on specific areas of the rug to e.g. eliminate odors emanating from animal or food droppings. A free flowing composition, like salt, would not have these properties. The present composition maintains these lazy flow characteristics and bridging properties over a long period of time and at elevated temperatures as described above.

The powdered composition is designed to be applied to the carpet and vacuumed, thereby resulting in deodorizing effects both to the rug and room. The composition of the present invention is also characterized by imparting excellent antistatic and anti-soiling effects to the carpet.

DETAILED DESCRIPTION OF THE INVENTION

The inorganic salt contemplated herein is selected from sulfates, bicarbonates and chlorides, particularly the alkali metal and alkaline earth metal salts thereof. Mixtures of one or more of these materials may be employed. This inorganic salt is used in a major amount in respect to each of the individual components of the composition, i.e. is used in amounts greater than any other individual component in the blend. Generally, this inorganic salt is used in an amount of about 50 to about 98 wt %, based upon the total weight of the carpet treating composition. Preferably this salt is used in an amount between about 75 to about 95 wt %, based upon the weight of the total composition.

The fragrances are selected from various volatile odorous agents, including essential oils, aromatic chemicals and the like. A great variety of these materials are known to those skilled in the perfuming arts and these materials may comprise, for example, one or more natural or synthetic aromatic agents or mixtures thereof. Thus, the present invention contemplates various fragrances or perfumes, such as essential oils having a floral bouquet, or a citrus, herbal or spice fragrance, etc. This material is employed in the composition in amounts effective to impart deodorizing characteristics to the carpet and room and the amount depends upon the strength of the fragrance used, etc. Generally the amount employed is an effective amount up to about 20%, based upon the total weight of the composition, the upper limit being primarily governed by economic considerations as well as by the nature of the fragrance used. Preferably the fragrance used in an amount of about 0.5 to about 5.0 wt %, based upon the weight of the entire composition.

Any of the well-known natural and synthetic zeolite materials may be used in the present composition. These zeolites are a class of synthetic aluminum silicates that can be hydrated of the type:

$$Na_2O \cdot Al_2O_3 \cdot mSiO_3 \cdot xH_2O.$$

These compounds have been disclosed in detail in R.F. Gould "Molecular Sieve Zeolites-I", Advances in Chemistry Series 101, American Chemical Society, Washington, D.C. 1971. Particularly important representatives are the zeolites of the so-called A-type, which are synthetic zeolites of the Na-Al-silicate type of the chemical formula (idealized): $Na_{12}[(AlO_2)_{12}(SiO_2)_{12}] \cdot xH_2O$, or put differently, $Na_2O:Al_2O_3:SiO_2 \approx 1:1:2$ with $AlO_2:SiO_2$-ratios about 12:12, i.e. put precisely between 1:0.5 to 1:2.5, especially between 1:0.8 to 1:1.5 (cf. R.F. Gould, loc. cit., pp. 10 and 12 as well as 22 and 23). The $Na_2O:SiO_2$ ratios of these zeolites lie between about 0.2 and 2.0 (cf. German Pat. No. 1,038,017). The teachings of these publications are incorporated by reference herein.

Such zeolite materials have been found to exhibit excellent antistatic and rheological control properties, as well as anti-soiling effects when employed in the carpet cleaning compositions of the present invention. These zeolite materials play an important role in the composition by contributing to a great extent to the lazy non-free flowing properties of the powder and producing the so-called "bridging" properties described above. Also, this material contributes to maintain the rheological properties of the composition stable over a long period of time and at elevated temperatures up to about 120° F. This is a key advantage over similar compositions which do not have this zeolite component, such as the aluminum oxide containing components described above.

An example of a specific zeolite is a molecular sieve zeolite type designated ZB-100 which is the sodium form of a type A zeolite having a crystalline structure produced by Union Carbide Corp. This material has a medium particle size of 3-5 microns and in which about 4% of the particles have a micron size greater than 10 microns.

The zeolite component is used in amounts sufficient to control the rheological properties of the composition such that with the other ingredients, the critical flow value of the blend is as described above and also this material is employed in amounts sufficient to impart antistatic properties to the composition. Thus, the zeolite material is used in amounts sufficient to acheive these dual effects.

Generally, the zeolite material is used in an amount of about 0.5 to about 30.0 wt % and preferably in amounts of about 1.0 to about 10.0 wt %, both weight ranges based upon the total weight of the composition.

The agglomerating liquid may be any non-fragrant liquid which imparts agglomerating effects to the composition by restricting the flow of the powder. In other words, this liquid is such that when added to a powder that is normally free flowing serves to restrict this free flowing property so that the composition is deposited in amounts substantially less than if it were free flowing. The term "free flowing" means the unrestricted flow of the powder from the container. The liquid agglomerating agent of the present invention serves to prevent this free flowing phenomenon and helps to control the critical flow value of the blend to between about 5.0 and about 30.0 g when stored in the closed container at elevated temperatures for at least 30 days as described above.

A variety of various agglomerating agents may be used as long as they are substantially non-fragrant (to distinguish over liquid perfumes). Obviously, the agglomerating agent should not be significantly malodorous or such as to counteract the fragrance imparting capacity of the composition. Examples of such liquid agglomerating agents are diethyl phthalate which has a boiling point of 158° C. at 10 mm Hg, dimethyl phthalate, various glycols, such as ethylene glycol, diethylene glycol, propylene glycol, dipropylene glycol, polyalkylene glycols, cosmetic fluids (e.g. Humble Exxon cosmetic fluids) and various liquid surfactants, such as nonionic surfactants, e.g. Tergitols, (e.g. Tergitol 15-S-9, Union Carbide Corporation), liquid Pluronics, e.g. Pluronic L-61 BASF-Wyandotte Corp., Pluracol W. 170 BASF, quaternary ammonium compounds such as N-alkyl ($C_{18}$92%, $C_{16}$8%)-N-ethyl morpholinium ethyl sulfates and also water may be used.

The liquid agglomerating agent is used in amounts sufficient to exert an agglomerating effect on the composition and is generally used in an amount up to about 20.0 wt %, the most preferred range being from about 0.25 to about 5.0 wt %, both ranges being based upon the total weight of the composition.

Other auxiliary agents may be employed in the composition, such as additional antistatic agents, subliming agents, anti-microbial agents, cleaning agents, (e.g. various anionic, nonionic, cationic and ampholytic detergents) as well as various fragrance volatility control agents. Solid agents such as starch may also be employed as a filler or auxiliary flow control agent. These materials may be used in the composition in amounts effective to accomplish their primary functions.

In preparing the blend of the aforementioned ingredients to produce the final powdered carpet treating composition, various methods may be used. Thus, all of the dry powdered ingredients may be placed into a Munson rotary batch blender while it is operating and mixed for approximately five minutes. Then the fragrance and agglomerating liquid may be added generally by means of a spray nozzle and the material mixed until uniformly blended. In place of the Munson blender, a Patterson Kelley twin shell blender or a Marion ribbon blender may be used. In accordance with the blending procedure of the present invention, it is preferred to add the fragrance and other liquids when all of the dry components have been first blended to obtain the optimum properties discussed above.

In respect to applying the composition to the carpet, the carpet treating composition can be applied from a shakeable canister or container having a top that contains openings whereby the product may be dispensed. The hole size and the number of holes may vary and the top may have a closure that can regulate the number of holes being opened at any time. The amount of product discharged can thus be regulated by both the hole openings as well as the rheological or flow properties of the powder itself.

The container used to dispense the material may be made of plastic material including polyethylene, polypropylene or polyacrylate or combinations thereof. The container may also be cardboard based and preferentially should be of a barrier nature i.e. aluminum foil inside and outside, or wax-coated or laminated.

The product is discharged from the container onto the carpet surface. During subsequent vacuuming the product in part becomes spread throughout the carpet surface and in part into the vacuum cleaning bag. Thus, the carpet, room and the vacuum cleaner play an integral part in deodorization. The amount of composition applied to the carpet depends a great deal upon the particular formulation, strength of the perfume, etc., but powder compositions applied to the carpet at a rate of as low as about 0.3 g per square feet of carpeting or less in some instances is sufficient to deodorize the rug and room.

By the term "deodorizing composition" as used herein is meant a composition which masks, neutralizes, reduces or otherwise overcomes malodors present in the carpeting, including pet or smoking odors. The deodorizng composition of the present invention also masks, neutralizes, reduces or otherwise overcomes musty vacuuming odors when the composition is removed from the carpet by vacuuming, rendering both the carpet and vacuuming bag with a refreshing and pleasant scent.

The composition of the present invention also serves to greatly reduce the static electricity of carpets when applied thereto, principally because of the antistatic properties of the zeolite material. The antistatic values of the rug are defined as the change in electrical charge on a carpet surface after application of the composition of the invention and after the powdered composition has been removed from the carpet as measured by A Simco electrostatic locator (Simco Corp. Model type SS-2).

The composition of the present invention also imparts anti-soiling effects to the carpet as measured by the resoiling effect. For the purpose of the present invention, this resoiling effect is defined as the property imparted to carpeting after treatment with the composition which results in a rate of soil deposition different from that obtained in the absence of such treatment. According to the present invention, the claimed composition has the capacity to reduce the soiling capacity of the carpet when applied thereto. This may be due primarily to the zeolite component.

The composition of the present invention has not only stable rheological properties but tends to "hold" those fragrances which have higher volatility parameters than powdered compositions with unstable rheological properties and this is partially due to the zeolite component as well as the agglomerating agent. However, when the powdered deodorizng composition is sprinkled onto the carpeting, the composition tends to give up the fragrance more readily than prior art compositions, such as those containing aluminum oxide, as described above. These dual properties make for a composition which can be stored under adverse conditions at elevated temperatures e.g. as high as 120° F., without losing its fragrance effects, while at the same time is capable of readily giving off the fragrance when scattered on a carpet. This combination of properties is very desirable in the carpet treating field.

As mentioned previously, the powdered carpet treating composition of the present invention maintains stable rheological properties under adverse conditions. The critical flow value of the blend as defined above, is broadly between about 5.0 and 30.0 g. In practice, the critical flow value is usually between about 10.0 and 25.0 g and preferably between about 11.0 and 21.0 g when stored in a closed container at temperatures up to about 120° F. for at least 30 days. This property represents one of the most significant features of the present invention and is a significant advance over the heretofore known carpet treating formulations of the type illustrated by U.S. Pat. No. 4,161,449 to Smith et al.

The following examples will further illustrate some specific embodiments of the invention. In these examples, all of the figures are given in percent by weight, unless otherwise specified.

EXAMPLE I

The following two formulations were prepared according to the present invention and the rheological properties of the composition were studied, both initially and after storage in a closed container for 30 days at various temperatures. Also, the weight loss of the compositions were measured at various temperatures.

| Formulations % by wt | #1 | #2 |
|---|---|---|
| Sodium Sulfate | 50.0 | 68.5 |
| Fine Sodium Bicarbonate | — | 26.0 |
| #5 Sodium Bicarbonate | 44.5 | — |
| Zeolite ZB-100 | 3.0 | 3.0 |
| Diethyl Phthalate | 1.0 | 1.0 |
| Fragrance (liquid) | 1.5 | 1.5 |

* The sodium sulfate employed is anhydrous sodium sulfate which is a free flowing crystalline powder substantially free of lumps.

The fine sodium bicarbonate component described in the Table is such that 95% passes through a 230 U.S. screen mesh.

The No. 5 sodium bicarbonate is a coarse granular material such that only about 20% passes through U.S. standard screen No. 100.

* The zeolite ZB-100 in the above formulations is the sodium form of the type A zeolite crystal structure. It is an alkaline metal aluminum silicate having a medium particle size of 3–5 microns and is such that about 4% of the composition has a particle size of greater than 10 microns. This material is purchased from Union Carbide Corp.

The diethyl phthalate is a perfumery grade oily liquid having a specific gravity of 1.115–1.119 at 25° C. and is odorless and colorless.

The above formulations were prepared as previously discussed by first mixing all the dry ingredients together and blending in a blender for about 5 minutes, then the liquid fragrance and diethyl phthalate was added via a spray nozzle and the blend further mixed for 5 minutes until the batch was uniform. The product was then placed in containers and the initial rheological properties were tested after the preparation and the material was then stored in a closed container to conduct the aging studies and the rheological properties and weight loss as discussed below.

The following tests were performed to determine the rheological properties of formulations 1 and 2 under varying conditions:

| Formulations | #1 | #2 |
|---|---|---|
| Rheological Properties[1] | | |
| Initial | 8.0 g | 11.0 g |
| Initial Density (g/cc) | | |
| Loose | 1.00 | 1.00 |
| Packed | 1.28 | 1.38 |
| AGING STUDIES ON RHEOLOGICAL PROPERTIES - (30 Day Storage) | | |
| 1. Weight loss % (filled closed containers) | | |
| Amb RT | 0.13 | 0.16 |

-continued

| Formulations | #1 | #2 |
|---|---|---|
| 105° F. | 0.36 | 0.35 |
| 120° F. | 0.40 | 0.62 |
| 2. Rheological Studies[(1)] (100 g initial charge) | | |
| Amb RT | 11.00 g | 13.00 g |
| 105° F. | 9.00 g | 13.00 g |
| 120° F. | 10.00 g | 13.00 g |

[(1)]The rheological or flow properties of the composition were measured by perceiving the rate of flow of the composition through a specified series of openings from a given size container (100 g) and given fill. Specifically, 100 g of the composition is filled into a container 2.5" in diameter by 5.5" in height having four holes, each approximately 0.31" in diameter inscribed in a 1" circle. The container is inverted successively 5 times and the amount of material in grams dispensed is determined. This test will be subsequently referred to as Test A.

It can be seen from the above that the compositions exhibit excellent flow properties at elevated temperatures over a long period of time and fall well within the critical flow value parameters previously discussed.

EXAMPLE II

The following formulations were prepared and rheological studies carried out.

| Formulations % by wt | #3 | #4 |
|---|---|---|
| Sodium Sulfate | 75.5 | 68.00 |
| Sodium Bicarbonate | 20.00 | 20.00 |
| #4A Zeolite[(1)] | 2.00 | 10.00 |
| Fragrance | 1.50 | 1.00 |
| Water | 1.00 | 1.00 |
| Densities | | |
| Loose[(2)] | 1.19 | 1.06 |
| Tamped[(3)] | 1.42 | 1.38 |
| Rheology | | |
| Test A | 17 g | 13 g |
| Test B | 15 g | 23 g |

[(1)]#4A Zeolite is an alkaline metal aluminum silicate of a type A zeolite crystalline structure sold under the trade name of Zeolite ZB-100 by Union Carbide.
[(2)]100 g sample poured through a 4" funnel into 250 ml volumetric cylinder. Density = weight/volume.
[(3)]As (2) except cylinder gently tamped for 30 seconds (or no apparent visual change in volume).
[(4)]The rheological test was carried out initially after preparation of the composition by the blending technique described in Example 1. These flow characteristics were tested at room or ambient temprature and the composition exhibited excellent non-free flowing properties falling within the critical flow limitation previously described.
Test A is the same 5x inversion test described in Example I. The Test B involves testing the flow properties of the composition by inserting 100 g of the composition in a container as described in Example I and shaking the container in a side-to-side motion in a horizontal position (simulating the way it is used by the consumer) for five seconds and the weight of the product dispensed was ascertained.

EXAMPLE III

The following formulation was prepared and blended as described in the previous Examples to illustrate that a variety of liquid agglomerating agents in combination with a fragrance may be employed.

| Formulation % by wt | | #5 |
|---|---|---|
| 4A Zeolite | | 1.00 |
| Sodium Bicarbonate | | 25.00 |
| Liquid Blend[(1)] | | 4.00 |
| Sodium Sulfate | | 70.00 |
| [(1)]Water | 21.0% | |
| Fragrance | 37.5% | |
| Tergitol 15-S-9 (nonionic surfactant | 4.0% | % by wt |
| N-Alkyl ($C_{18}$92%,$C_{16}$8%) N-ethyl morpholinium ethyl sulfates | 37.5% | |

-continued

| Density Characteristics | |
|---|---|
| Loose (g/cc) | 1.00 |
| Tamped (g/cc) | 1.28 |

DETERMINATION OF THE RHEOLOGICAL PROPERTIES OF THE COMPOSITION AT AMBIENT OR ROOM TEMPERATURE

| | |
|---|---|
| Shake Test A (same as in Example I) | 18 g |
| Shake Test B (same as in Example II) | 20 g |

Both Test A and Test B were carried out shortly after the composition was prepared and packaged in the container.

EXAMPLE IV

| Formulations parts by wt | #6 |
|---|---|
| Sodium Sulfate | 51.5 |
| #5 Sodium Bicarbonate | 40.0 |
| FD-1 (50/50 ZB-100/Sodium Bicarbonate) | 3.0 |
| Catapal SB* | 1.5 |
| Fragrance | 1.5 |
| Diethyl phthalate | 1.0 |
| Rheological Properties | |
| (Test A at ambient temperature, after composition was initially made up) | 9.0g |
| Initial Density (loose) | 1.00 |
| g/cc (packed) | 1.28 |

*aluminum oxide with 4 moles of water

EXAMPLE V

The following demonstrates the rheological effects of adding varying amounts of water to the powdered composition.

| Formulations parts by weight | #7 | #8 | #9 |
|---|---|---|---|
| Zeolite ZB-100 | 10.0 | → | → |
| #5 Sodium Bicarbonate | 20.0 | → | → |
| Sodium Sulfate | 68.5 | → | → |
| Fragrance | 1.5 | → | → |
| Water (% by wt added) | 10 | 20 | 30 |
| Rheological Properties (at ambient room temperature Test A) | 10 g | 6 g | NF* |

*The term "NF" means that the composition is non-free flowing and significantly less of the composition is deposited as opposed to the case when only 10 or 20% water is used.

COMPARATIVE EXPERIMENTS

The following experiments are designed to show the effects of certain ingredients in various carpet treating compositions.

COMPARATIVE EXPERIMENT I

The following formulations were prepared with a view towards determining the various weight loss characteristics of zeolite based formulations as opposed to the same composition replaced by aluminum oxide, said formulations being prepared without a liquid agglomerating agent.

| Formulations % by wt | #10 | #11 |
|---|---|---|
| Sodium Sulfate | 68.50 | 68.50 |

-continued

| Formulations % by wt | #10 | #11 |
|---|---|---|
| Sodium Bicarbonate | 20.00 | 20.00 |
| Unmodified Starch | 7.00 | 7.00 |
| #4A Zeolite | 3.00 | — |
| Fragrance | 1.50 | 1.50 |
| Catapal SB | — | 3.00 |

The above formulations were examined for weight loss and flow or rheological properties under a variety of conditions using Test A and Test B as previously described. The results of these tests are shown below.

TABLE 1

| Formulations | #10 (3% 4A Zeolite) | #11 (Identical to Form. 10 except with 3% Catapal SB) |
|---|---|---|
| Open Dish[1] | | |
| % weight loss | | |
| 2 hours | 0.13% | 0.34% |
| 2 days | 0.42% | 0.66% |
| Sealed Container Storage[2] | | |
| % weight loss | | |
| After 4 wks storage | | |
| room temperature | 0.25% | 0.19% |
| 105° F. | 0.83% | 0.78% |
| 120° F. | 1.18% | 1.40% |

[1]Product placed in an open aluminum dish and stored at ambient room temperature. Evaluation made after two hours and two days.
[2]Product placed in a foil wrapped cardboard container and sealed with a closed perforated dispensing top. Weight loss comparisons and rheological properties were measured.

Rheological Properties:

| | | |
|---|---|---|
| Initial (at ambient temperature) | Lazy powder | Lazy powder |
| 2 days | Not free flowing | Dry, dusty, free flowing |

| Rheological Properties After Storage (Test A and B) | Test A | Test B |
|---|---|---|
| At ambient (room) temperature | | |
| Zeolite 4A (25 days) (Form. 10) | 12 g | 17 g |
| Catapal SB (29 days) (Form. 11) | 12 g | 16 g |
| At 105° F. | | |
| Zeolite 4A (25 days) | 10 g | 10 g |
| Catapal SB (29 days) | 14 g | 30 g |
| At 120° F. | | |
| Zeolite 4A (25 days) | 13 g | 18 g |
| Catapal SB (29 days) | Dusty, free flowing | Dusty, free flowing |

It is apparent from the above that the zeolite based compositions are far superior to those of the aluminum oxide based compositions, even when a liquid agglomerating agent is not present. The weight loss for the zeolite based composition is also significantly less than the similar composition containing aluminum oxide.

COMPARATIVE EXPERIMENT II

The following Experiment shows that zeolite has a capacity to give a more efficient fragrance release than that of aluminum oxide.

| | % | Ingredient |
|---|---|---|
| Formulation #12 | | |
| | 85 | Zeolite ZB-100 |
| | 15 | Fragrance Oil |
| Formulation #13 | | |
| | 85 | Aluminum Oxide (Catapal SB) |
| | 15 | Fragrance Oil |

Approximately 8.0 g were placed in aluminum weighing dishes and weighed to two places. The weight loss was measured periodically. The following is a summary of the weight loss vs. time.

| Formulation #12 | | Formulation #13 | |
|---|---|---|---|
| Time/Days | % Fragrance Loss | Time/Days | % Fragrance Loss |
| 3 | 33.9 | 3 | 33.9 |
| 7 | 48.0 | 7 | 35.0 |
| 20 | 67.3 | 20 | 40.8 |

COMPARATIVE EXPERIMENT III

The following Tables illustrate the effects of various fragrance levels of the flow properties of aluminum oxide and zeolite powder systems.

TABLE 2

The Effect of Fragrance Concentration on the Rheological Properties of Non-Zeolite Powder Systems

| Formulations parts by weight | #14 | #15 | #16 | #17 | #18 | #19 | #20 | #21 |
|---|---|---|---|---|---|---|---|---|
| Sodium Sulfate | 68.5 | → | → | → | → | → | → | → |
| Sodium Bicarbonate | 20.0 | → | → | → | → | → | → | → |
| Starch | 7.0 | → | → | → | → | → | → | → |
| Aluminum Oxide Monohydrate | 3.0 | → | → | → | → | → | → | → |
| Fragrance | 0.0 | 0.25 | 0.50 | 0.75 | 1.0 | 1.25 | 1.50 | 1.75 |
| Flow Characteristics | FF | FF | FF | FF | NFF | NFF | NFF | NFF* |
| Loose Density (g/cc) | 1.28 | 1.31 | 1.31 | 1.25 | 1.11 | 1.04 | 1.00 | 0.98 |

*Ff - Free Flowing
NFF - Non-Free Flowing (falls within critical flow value range previously described)

TABLE 3

The Effect of Various Fragrance Levels on the Rheological Properties of a Zeolite Powder System

| Formulations parts by weight | #22 | #23 | #24 | #25 | #26 |
|---|---|---|---|---|---|
| Sodium Sulfate | 68.5 | 68.5 | 68.5 | 68.5 | 68.5 |
| Sodium Bicarbonate | 20.0 | 20.0 | 20.0 | 20.0 | 20.0 |
| Zeolite ZB-100 | 10.0 | 10.0 | 10.0 | 10.0 | 10.0 |
| Fragrance | 0.5 | 1.0 | 1.5 | 2.0 | 3.0 |
| Flow Test A | 15 g | 14 g | 18 g | 18 g | 18 g |
| Densities (g/cc) | | | | | |
| Loose | 1.08 | 1.08 | 1.16 | 1.11 | 1.19 |
| Packed | 1.43 | 1.43 | 1.43 | 1.47 | 1.47 |

It can be seen by the above, that it requires more fragrance to render the non-zeolite powder system of the prior art into a non-free flowing state, even when starch is employed with the aluminum oxide component, as opposed to that of a zeolite powder system.

COMPARATIVE EXPERIMENT IV

The following shows the results of zeolite on the flow properties of a basic non-fragrance powdered composition.

TABLE 4

A Comparison of Zeolite ZB-100 and Starch on Powder Rheological Properties (Non-Fragranced)

| Formulations parts by weight | #27 | #28 | #29 | #30 | #31 | #32 | #33 | #34 |
|---|---|---|---|---|---|---|---|---|
| Sodium Sulfate | 70 | 70 | 70 | 70 | 70 | 70 | 70 | 70 |
| Sodium Bicarb. | 20 | 20 | 20 | 20 | 20 | 20 | 20 | 20 |
| Zeolite 2B-100 | — | 1 | 2 | 5 | 10 | 20 | — | — |
| Starch | — | — | — | — | — | — | 10 | 20 |
| Flow Test A (average) | 90g | 76g | 28.5g | 24g | 16.7g | 11.7g | 99g | 95g |

This shows that the zeolite component is much more influential in governing the flow properties of the composition than starch. Note that when even 2% by weight of zeolite is added to a starch-free composition, the composition exhibits non-free flowing properties within the critical flow value range previously described, whereas as much as 20 g of starch added to a zeolite-free composition still does not render the composition non-free flowing to the extent contemplated in the present invention.

COMPARATIVE EXPERIMENT V

The following formulation represents a comparison between the rheological properties of a starch zeolite formulation as opposed to a similar starch-aluminum oxide powder formulation at elevated temperatures.

TABLE 5

Comparison of Rheological Properties of Starch/Aluminum Oxide Powder Formulations

| Formulations % by wt | #35 | #36 |
|---|---|---|
| Storage 120° F. | | |
| Sodium Sulfate | 68.5 | 68.5 |
| Sodium Bicarbonate | 20.0 | 20.0 |
| Starch | 7.0 | 7.0 |
| Aluminum Oxide . $H_2O$ | 3.0 | — |
| Zeolite ZB-100 | — | 3.0 |
| Fragrance | 1.5 | 1.5 |
| Days | 22 | 30 |
| Powder Rheology | Free Flowing | Non-Free Flowing |

The above comparison shows that an aluminum oxide based composition used in the prior art as previously described is far inferior to applicants' zeolite based compositions, even though a liquid agglomerating agent is not employed therein. Note that the aluminum oxide containing composition is free-flowing after storage in a closed container after 22 days, whereas applicants' composition exhibits non-free flowing characteristics having the critical flow value of between 5 and 30 g as previously described, even after 30 days.

COMPARATIVE EXPERIMENT VI

The following tests were used to measure the antistatic properties of a composition of the present invention, viz. formulation #2 in Example I.

General Test Procedure

According to the method employed herein, the measurement of the electrostatic charge produced on synthetic carpets, is made indirectly by measuring the "electric field" or "electric potential" that the charge produces in its surroundings. The instrument used to measure the charge is a Simco Electrostatic Locator Type SS-2. A charge is produced on a test swatch of nylon carpeting by rubbing with a plastic wand. The strength of the charge is measured and recorded. The relative humidity and temperature are also recorded. In order to measure the antistatic properties of a carpet powder, the powder is sprinkled on a carpet swatch, the carpet rubbed with the wand or a plastic bottle, such as polyvinyl chloride, and the charge measured. This reading is compared with the charge obtained without the powder on the rug and in this way the relative antistatic properties of the powder determined. The lower the reading or reduction in charge between treated and untreated carpets the better the antistatic properties of the test powders. In order to produce stable electrostatic charges, humidity readings of about 40% or lower are necessary.

Specific Test Procedure

To carry out the specific test concerning the effects of formulation #2 the relative humidity and temperature was first recorded and a weighed nylon carpet swatch 6"×6" was rubbed with a plastic wand. The charged rug was then measured with the electrostatic locator and the charge in volts for the untreated carpet was recorded.

Next, the powder formulation #2 was sprinkled onto the carpet, brushed in lightly and the treated swatch weighed. Then, the charge in volts for the treated swatch was measured.

Finally, the treated swatch was vacuumed using a 5" nozzle of a Hoover canister type vacuum cleaner. After vacuuming, the weight of the rug was determined and the residual powder estimated. The rug was rubbed with the wand and the stable charge measured. This is recorded as the charge produced on a treated rug after vacuuming.

The results of the above measurements are as follows:

ELECTROSTATIC MEASUREMENTS

Relative Humitidy = 33%   Temperature = 72° F.
Test powder - Formulation #2

| Carpet Swatch | Test Powder | Electrostatic Charge/Volts |
|---|---|---|
| Untreated | None | 2200 |
| Treated | 7.5 gms | 100 (maximum unstable) |
| Treated-vacuumed | 2.5 gms | 100 |

It is apparent from the above that formulation #2 prepared according to the present invention has additionally excellent antistatic properties, capable of reducing the capability of the rug to produce a charge from 2200 volts to 100 volts.

COMPARATIVE EXPERIMENT VII

The following tests show the effectiveness of zeolite ZB-100 as an antistat compared to the alumina salt catapal SB, using the same test procedure employed in Example VI.

Relative Humidity 38%    Temperature 78° F.
Test Powder
  A. Zeolite ZB-100 (Supplied by Union Carbide)
  B. Catapal SB (Supplied by Conoco Chemical Co.)

| Carpet Swatch | Test Powder | Electrostatic Charge/Volts |
|---|---|---|
| Untreated | None | 800 |
| Treated | 2 gms of A | 80 |
| Untreated | None | 600 |
| Treated | 3 gms of B | 220 |

This test illustrates the effectiveness of zeolite ZB-100 as an antistatic powder as well as its superiority to catapal SB. In this connection, the electrostatic charge of the treated rub was measured without vacuuming.

In summary, it can be seen that the powdered carpet treating composition of the present invention exhibits unusually stable rheological properties and fragrance retention capabilities over a long period of time and at elevated temperatures. Also, the compositions have excellent antistatic properties as demonstrated above.

In respect to the various test procedures employed herein, such as test A to measure the critical flow value, this test was performed by hand making an effort to shake the various containers with the same degree of force in all instances, however, such test procedures have also been duplicated by a simple mechanical device designed to eliminate any possibility of human error. Thus, a support with a rectangular base, a three-pronged clamp, a clamp holder and a tray to collect powder was employed. The container was inserted into the three-pronged clamp, which clamp is connected to a sleeve which serves to rotate the container by hand at 180° at a speed of approximately 15 rpm. Such 180° rotation is carried out 5 times so as to satisfy the 5 times rotation inversion test and the amount of powder collected in the tray, located at the bottom of the container was measured. The results achieved by such a mechanical procedure correspond very closely to those results demonstrated in the specific Examples.

Finally, it must be emphasized that the preceding specific embodiments are illustrative of the practice of the invention. It must be understood, however, that other expedients known to those skilled in the art, as disclosed herein, may be employed without departing from the spirit of the invention or the scope of the appended claims.

What is claimed is:

1. A powdered carpet treating composition having stable rheological properties consisting essentially of a blend of:
   (a) a major amount in respect to each of the individual components in the composition of an inorganic salt selected from the group consisting of sulfates, bicarbonates, chlorides and mixtures thereof;
   (b) an effective deodorizing amount of a fragrance;
   (c) an antistatic and rheological control agent selected from the group consisting of natural and synthetic zeolites, said material being used in an effective amount sufficient to impart antistatic properties to the composition and control the rheological properties of the composition; and
   (d) an effective agglomerating amount of a substantially non-fragrant liquid agglomerating agent; wherein
   (1) a weight ratio of component (c) to component (d) is from between about 30.0:1.0 and about 0.5:1.0;
   (2) the critical flow value of the blend is from between about 5.0 and about 30.0 g when stored in a closed container at temperatures up to about 120° F. for at least 30 days; and
   (3) the effective fragrance imparting properties of the composition is maintained for at least 30 days when stored in a closed container at temperatures up to about 120° F.

2. A composition according to claim 1 wherein the inorganic salt is present in an amount of about 50 to about 98 wt%.

3. A composition according to claim 1 wherein the inorganic salt is present in an amount of about 75.0 to about 95.0 wt%.

4. A composition according to claim 1 wherein the fragrance is present in an effective deodorizing amount up to about 20.0 wt%.

5. A composition according to claim 1 wherein the fragrance is present in an amount of about 0.5 to about 5.0 wt%.

6. A composition according to claim 1 wherein the antistatic and rheological control agent is present in an amount of about 0.5 to about 30.0 wt%.

7. A composition according to claim 1 wherein the antistatic and rheological control agent is present in an amount of about 1.0 to about 10.0 wt%.

8. A composition according to claim 1 wherein the liquid agglomerating agent is present in an amount up to about 20.0 wt%.

9. A composition according to claim 1 wherein the liquid agglomerating agent is used in an amount of about 0.25 to about 5.0 wt%.

10. A composition according to claim 1 wherein the inorganic salt is present in an amount of about 50.0 to about 98.0 wt%, the fragrance is present in an effective deodorizing amount up to about 20.0 wt%, the antistatic and rheological control agent is present in an amount of about 0.5 to about 30.0 wt % and the liquid agglomerating agent is present in an effective agglomerating amount up to about 20.0 wt%.

11. A composition according to claim 1 wherein the inorganic salt is present in an amount of about 75.0 to about 95.0 wt%, the fragrance is present in an amount of about 0.5 to about 5.0 wt%, the antistatic and rheological control agent is present in an amount of about 1.0 to about 10.0 wt% and the liquid agglomerating agent is present in an amount of about 0.25 to about 5.0 wt%.

12. A composition according to claim 1 wherein the inorganic salt is a mixture of 68.5 wt% of sodium sulfate and 26.0 wt% of sodium bicarbonate, the zeolite is present in an amount of 3.0 wt%, the agglomerating agent is diethyl phthalate present in an amount of 1.0 wt%, and the fragrance is present in an amount of 1.5 wt%.

13. A composition according to claim 1 wherein the critical flow value of the blend is from between about 10.0 about 25.0 g.

14. A composition according to claim 1 wherein the critical flow value of the blend is from between about 11.0 and about 21.0 g.

15. A method for imparting deodorizing and air-freshening characteristics to a carpet which comprises applying to the carpet an effective amount of a composition according to claims 1, 10, 11 or 12 thereafter removing said composition from the carpet.

16. A method for imparting deodorizing, antistatic and anti-soil redeposition characteristics to a carpet which comprises applying to the carpet from a shakeable canister, an effective amount of a composition according to claims 1, 10, 11 or 12 and removing said composition by means of a vacuum cleaner.

* * * * *

UNITED STATES PATENT AND TRADEMARK OFFICE
CERTIFICATE OF CORRECTION

PATENT NO. : 4,304,675
DATED : December 8, 1981
INVENTOR(S) : G. G. Corey and L. E. Paszek It is certified that error appears in the above-identified patent and that said Letters Patent are hereby corrected as shown below:

Column 1, line 66, "smith" should read -- Smith --.

Column 2, line 40, "room" should read -- rooms --.

Column 3, line 67, "which" should read -- with --.

Column 7, line 30, "A" should read -- a --.

Column 16, line 6, Claim 1, "a" should read -- the --.

Column 17, line 4, Claim 15, -- and -- should be inserted after -- 12 --.

Signed and Sealed this

Twenty-seventh Day of July 1982

[SEAL]

Attest:

Attesting Officer

GERALD J. MOSSINGHOFF
Commissioner of Patents and Trademarks